US008636718B2

(12) United States Patent
Sela et al.

(10) Patent No.: US 8,636,718 B2
(45) Date of Patent: Jan. 28, 2014

(54) METHOD OF ASSEMBLING A POSITIONING SENSOR AND ASSOCIATED WIRING ON A MEDICAL TOOL

(75) Inventors: Ran Sela, Tel Aviv-Jaffa (IL); Lior Sobe, Kadima (IL); Dan Seter, Haifa (IL)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 323 days.

(21) Appl. No.: 12/981,963

(22) Filed: Dec. 30, 2010

(65) Prior Publication Data

US 2012/0172842 A1 Jul. 5, 2012

(51) Int. Cl.
*A61M 25/00* (2006.01)
*H01R 43/20* (2006.01)
*B23P 17/04* (2006.01)

(52) U.S. Cl.
USPC .............................. 604/528; 29/428; 29/592.1

(58) Field of Classification Search
USPC ............ 604/528, 264; 29/592.1, 428; 607/19; 600/508
See application file for complete search history.

(56) References Cited

U.S. PATENT DOCUMENTS

| | | | |
|---|---|---|---|
| 6,233,476 B1 | 5/2001 | Strommer et al. | |
| 6,356,790 B1 * | 3/2002 | Maguire et al. | 607/102 |
| 6,498,944 B1 | 12/2002 | Ben-Haim et al. | |
| 6,788,967 B2 * | 9/2004 | Ben-Haim et al. | 600/424 |
| 6,972,575 B2 * | 12/2005 | Lambert et al. | 324/658 |
| 6,985,764 B2 * | 1/2006 | Mason et al. | 600/344 |
| 7,197,354 B2 | 3/2007 | Sobe | |
| 7,250,049 B2 | 7/2007 | Roop et al. | |
| 7,386,339 B2 | 6/2008 | Strommer et al. | |
| 7,706,891 B2 | 4/2010 | Hastings et al. | |
| 8,121,687 B2 * | 2/2012 | Jensen et al. | 607/17 |
| 2004/0097804 A1 | 5/2004 | Sobe | |
| 2005/0107688 A1 | 5/2005 | Strommer | |
| 2005/0197557 A1 | 9/2005 | Strommer et al. | |
| 2005/0261582 A1 * | 11/2005 | Becker et al. | 600/437 |
| 2006/0084852 A1 * | 4/2006 | Mason et al. | 600/344 |
| 2007/0055327 A1 * | 3/2007 | Esch et al. | 607/96 |
| 2007/0179575 A1 * | 8/2007 | Esch et al. | 607/96 |
| 2007/0265637 A1 * | 11/2007 | Andreas et al. | 606/108 |
| 2008/0161762 A1 * | 7/2008 | Stehr et al. | 604/264 |
| 2008/0255629 A1 * | 10/2008 | Jenson et al. | 607/19 |
| 2009/0177090 A1 * | 7/2009 | Grunwald et al. | 600/454 |
| 2009/0192412 A1 * | 7/2009 | Sela et al. | 600/585 |
| 2012/0130231 A1 * | 5/2012 | Ngo et al. | 600/424 |
| 2012/0172716 A1 * | 7/2012 | Sela et al. | 600/424 |
| 2012/0172717 A1 * | 7/2012 | Gonda | 600/424 |

* cited by examiner

*Primary Examiner* — Emily Schmidt
*Assistant Examiner* — Michael J Anderson
(74) *Attorney, Agent, or Firm* — Dykema Gossett PLLC (57) ABSTRACT

An elongate medical device having an axis comprises an inner liner, a jacket radially outward of the liner, a braid comprising metal embedded in the jacket, a sensor, and at least one wire electrically connected to said sensor. The at least one wire is one of: embedded in the jacket and optionally disposed helically around the braid; extending longitudinally within a tube which extends generally parallel to the device axis and wherein the tube is embedded in the jacket; and disposed within a lumen, wherein the lumen extends longitudinally within the jacket.

5 Claims, 8 Drawing Sheets

FIG. 16

METHOD OF ASSEMBLING A POSITIONING SENSOR AND ASSOCIATED WIRING ON A MEDICAL TOOL

BACKGROUND OF THE INVENTION a. Field of the Invention

The present disclosure relates to a method of manufacturing a catheter or other elongate medical device to reduce the stress induced on an electrical cable in the catheter or other elongate medical device.

b. Background Art

Many medical procedures require the introduction of specialized medical devices into and/or around the human heart. In particular, there are a number of medical procedures that require the introduction of specialized devices including, but not limited to, catheters, dilators, and needles to areas, such as into the atria or ventricles to access the inner surface of the heart, or into the pericardial sac surrounding the heart to access the epicardial or outer surface of the heart. Catheters, guidewires, and access sheaths or introducers have been used for medical procedures for a number of years.

It is typically necessary for introducers, guidewires, and catheters to exhibit a balance of flexibility and rigidity to be able to maneuver through the vasculature of a patient during the performance of medical procedures. In addition, it is desirable to reduce the stress induced on a catheter, introducer, or other elongate medical device during bending. In particular, it is desirable to reduce the stress induced on electrical wiring by bending of the medical device, as such stress may interrupt the functionality of sensors attached to such wiring.

There is therefore a need for a MPS-enabled elongate medical device and methods of manufacture thereof that minimize or eliminate one or more of the problems set forth above.

BRIEF SUMMARY OF THE INVENTION

One advantage of the methods and apparatus described, depicted, and claimed herein relates to a reduction in the stress experienced in or by wiring in a medical device that connects a positioning sensor (e.g., at a distal end) to a connector (e.g., at a proximal end) when the device is subjected to bending or deflection.

This disclosure is directed to an elongate medical device configured for use with a positioning system (i.e., the device includes a positioning sensor). The device has an axis and includes an inner liner, a jacket radially outward of the liner, a braid comprising metal embedded in the jacket, a sensor, and at least one wire electrically connected to the sensor. The at least one wire is incorporated in the device in at least one of the following ways: (i) the at least one wire is embedded in the jacket and may optionally be disposed helically about the braid; (ii) the at least one wire extends longitudinally within a tube which is embedded in the jacket; and (iii) the at least one wire is disposed within a lumen where the lumen extends longitudinally within the jacket. Through the foregoing, the stress experienced by the at least one wire, for example when the device is subjected to bending, is reduced, which in turn reduces the occurrence of breaks or the like either in the wire or at the connection node where the wire is connected to the sensor.

In another aspect, a method of fabricating an elongate medical device having an axis comprises the steps of providing an elongate liner having a distal end and a proximal end, surrounding the liner with a braid comprising metal, placing a positioning sensor over the braid at the distal end, disposing a longitudinally-extending element radially outward from the braid such that the element is generally parallel to the axis, applying an outer layer over the braid, the sensor, and the longitudinally-extending element, and subjecting the device to a reflow lamination process.

These and other benefits, features, and capabilities are provided according to the structures, systems, and methods depicted, described and claimed herein.

DETAILED DESCRIPTION OF THE INVENTION

Figure 1:
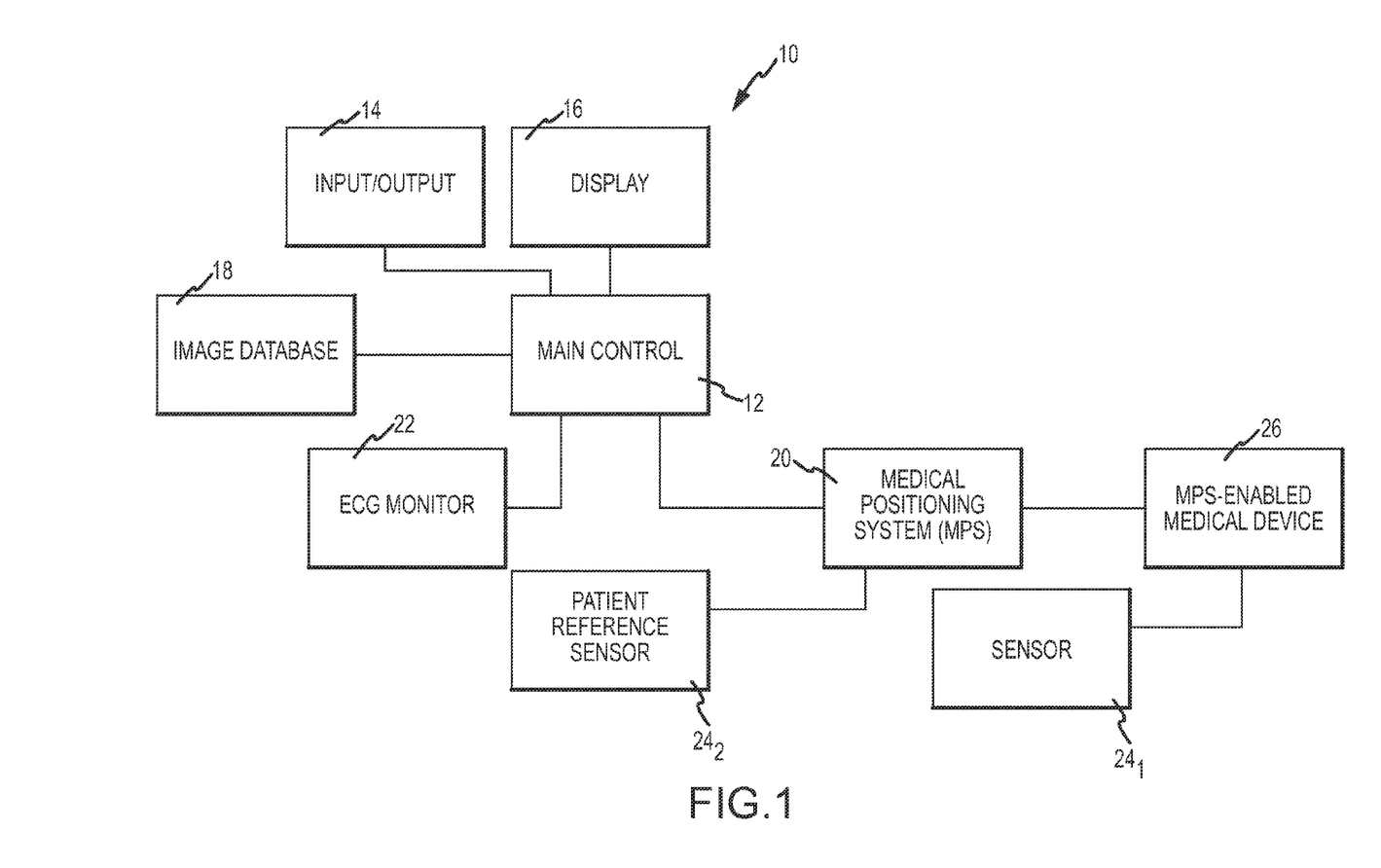
FIG. 1 is a schematic and block diagram view of a system incorporating an embodiment of an MPS-enabled elongate medical device.

Referring now to the drawings wherein like reference numerals are used to identify identical components in the various views, FIG. 1 is a diagrammatic view of a system 10 in which a position sensing elongate medical device such as a guidewire or catheter may be used. It should be understood that while embodiments will be described in connection with a magnetic field-based positioning system in a catheter-lab environment, this is exemplary only and not limiting in nature.

There is a desire to reduce a patient's exposure to x-rays, such as may be used in live fluoroscopy, at least for the purpose of navigating a medical device such as a catheter within the patient's body. Such a desire may be met by providing a medical device that includes a positioning sensor configured to cooperate with an external (i.e., external to the patient's body) positioning system that can determine the position of the device in three-dimensional space. With this position information, a navigation system can superimpose a representation of the medical device over a previously-obtained image (or series of images) of the region of interest in the patient's body. Accordingly, the clinician may use the superimposed imaging for navigation purposes rather than full time fluoroscopy. Thus, through the provision of a medical device with position sensing capability, the use of fluoroscopy may be reduced significantly (and the accompany X-ray exposure for the patient). The methods and apparatus described herein relating to medical positioning system (MPS)-enabled medical devices facilitate the reduction of the need for continuous exposure or extensive use of fluoroscopy for such purposes.

With continued reference to FIG. 1, system 10 as depicted includes a main electronic control unit 12 (e.g., one or more processors) having various input/output mechanisms 14, a display 16, an optional image database 18, a localization system such as a medical positioning system (MPS) 20, an electrocardiogram (ECG) monitor 22, one or more MPS location sensors respectively designated $24_1$ and $24_2$ (i.e., shown as a patient reference sensor), and an MPS-enabled elongate medical device 26 which itself includes one or more of the above-described MPS location sensors, shown in exemplary fashion as having one such sensors $24_1$.

Input/output mechanisms 14 may comprise conventional apparatus for interfacing with a computer-based control unit, for example, a keyboard, a mouse, a tablet, a foot pedal, a switch or the like. Display 16 may also comprise conventional apparatus.

Embodiments consistent with the invention may find use in navigation applications that use imaging of a region of interest. Therefore system 10 may optionally include image database 18. Image database 18 may be configured to store image information relating to the patient's body, for example a region of interest surrounding a destination site for medical device 26 and/or multiple regions of interest along a navigation path contemplated to be traversed by device 26 to reach the destination site. The image data in database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from ECG monitor 22. It should be understood that the foregoing are examples only and not limiting in nature. For example, the image database may also include three-dimensional image data as well. It should be further understood that the images may be acquired through any imaging modality, now known or hereafter developed, for example X-ray, ultrasound, computerized tomography, nuclear magnetic resonance or the like.

MPS 20 is configured to serve as the localization system and therefore to determine positioning (localization) data with respect to one or more of MPS location sensors $24_i$ (where i=1 to n) and output a respective location reading. The location readings may each include at least one or both of a position and an orientation (P&O) relative to a reference coordinate system, which may be the coordinate system of MPS 20. For example, the P&O may be expressed as a position (i.e., a coordinate in three axes X, Y and Z) and orientation (i.e., an azimuth and elevation) of a magnetic field sensor in a magnetic field relative to a magnetic field generator(s) or transmitter(s).

Figure 2:
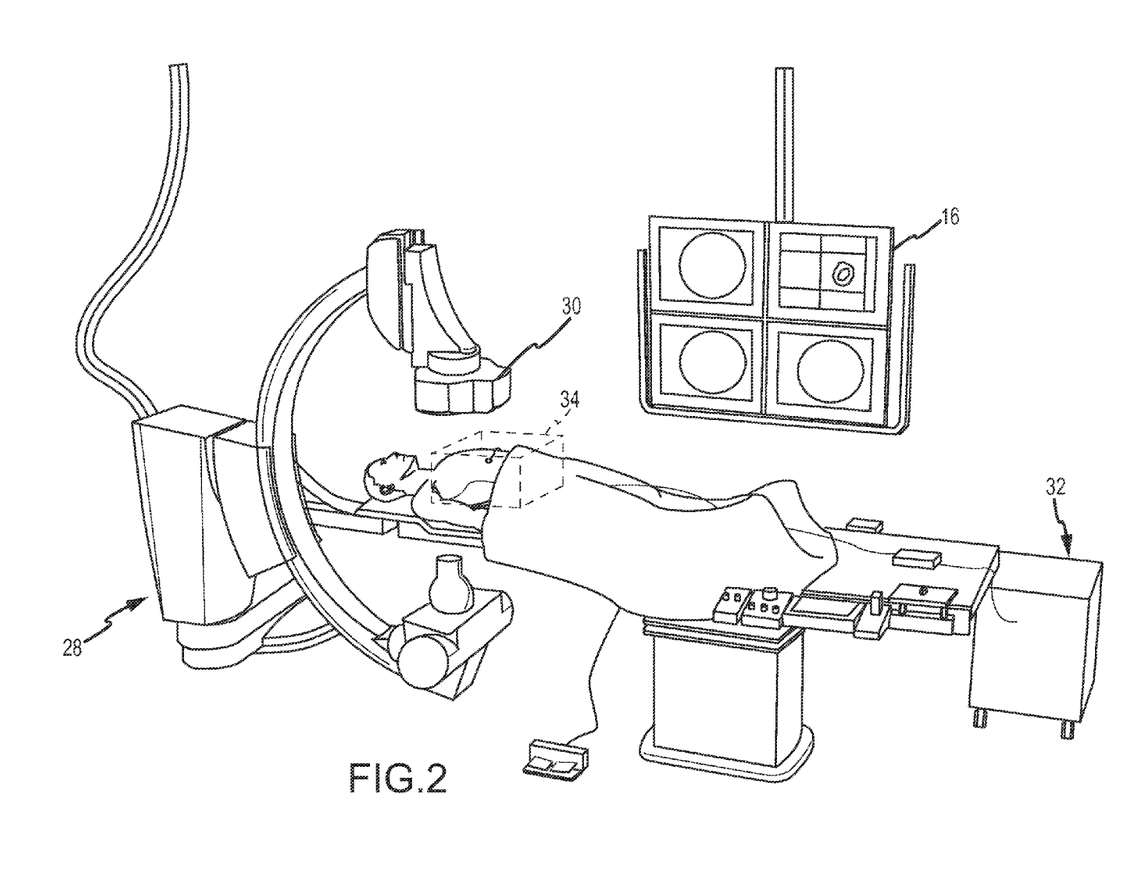
FIG. 2 is a diagrammatic view of the system of FIG. 1 in a catheter-lab environment.

MPS 20 determines respective locations (i.e., P&O) in the reference coordinate system based on capturing and processing signals received from the magnetic field sensors $24_i$ while such sensors are disposed in a controlled low-strength AC magnetic field (see FIG. 2). From an electromagnetic perspective, these sensors develop a voltage that is induced on the coil residing in a changing magnetic field, as contemplated here. Sensors $24_i$ are thus configured to detect one or more characteristics of the magnetic field(s) in which they are disposed and generate an indicative signal, which is further processed by MPS 20 to obtain a respective P&O thereof. Exemplary design features and manufacturing processes and methods for sensors $24_i$ and medical devices incorporating such sensors will be described in greater detail below in conjunction with FIGS. 3-12.

MPS sensor $24_1$, and optionally additional MPS sensors in further embodiments, may be associated with MPS-enabled medical device 26. Another MPS sensor, namely, patient reference sensor (PRS) $24_2$ (if provided in system 10) is configured to provide a positional reference of the patient's body so as to allow motion compensation for gross patient body movements and/or respiration-induced movements. PRS $24_2$ may be attached to the patient's manubrium sternum, a stable place on the chest, or another location that is relatively positionally stable. Like MPS location sensor $24_1$, PRS $24_2$ is configured to detect one or more characteristics of the magnetic field in which it is disposed wherein MPS 20 provides a location reading (e.g., a P&O reading) indicative of the PRS's position and orientation in the reference coordinate system.

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit 12 for ECG synchronized play-back of a previously captured sequence of images (cine loop) stored in database 18. ECG monitor 22 and ECG-electrodes may both comprise conventional components.

FIG. 2 is a diagrammatic view of system 10 as incorporated into an exemplary catheter laboratory. System 10 is shown as being incorporated into a fluoroscopic imaging system 28, which may include commercially available fluoroscopic imaging components (i.e., "Catheter Lab"). MPS 20 includes a magnetic transmitter assembly (MTA) 30 and a magnetic processing core 32 for determining location (P&O) readings. MTA 30 is configured to generate the magnetic field(s) in and around the patient's chest cavity, in a predefined three-dimensional space identified as a motion box 34. MPS sensors $24_i$ as described above are configured to sense one or more characteristics of the magnetic field(s) and when the sensors are in motion box 34, each generate a respective signal that is provided to magnetic processing core 32. Processing core 32 is responsive to these detected signals and is configured to calculate respective P&O readings for each MPS sensor $24_i$ in motion box 34. Thus, MPS 20 enables real-time tracking of each sensor $24_i$ in three-dimensional space.

The positional relationship between the image coordinate system and the MPS reference coordinate system may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in database 18), a registration step registering the MPS coordinate system and the image coordinate system may need to be performed so that MPS location readings can be properly coordinated with any particular image being used. One exemplary embodiment of an MPS 20 will be described in greater detail below in connection with FIG. 16.

For an MPS-enabled medical device 26, such as a catheter, to be tracked by a localization system such as MPS 20, electrical function of MPS sensors coupled with the device must be assured. As such, signal and power wiring associated with such sensors should be assembled in the medical device with a method that minimizes the stress induced on the wiring by bending of the medical device.

FIGS. 3-8 are isometric, exaggerated side views of a reflow mandrel assembly in various stages of build-up in a method of manufacture of a first embodiment and a second embodiment of an MPS-enabled elongate medical device 26. It should be understood that while radial "gaps" or clearances are shown in FIGS. 3-8 between the several layers of materials, this is done for clarity only to distinguish the separate layers.

Figure 3:
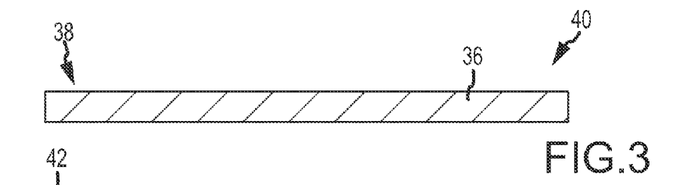
FIGS. 3-8 are isometric side views of a reflow mandrel assembly in various stages of build-up in a method of manufacture of a first embodiment and a second embodiment of an MPS-enabled elongate medical device.

FIG. 3 shows a mandrel 36 having a distal end portion 38 and a proximal end portion 40. Mandrel 36 may be circular in radial cross-section and have a desired length, in view of the elongate medical device to be made.

Figures 4, 5, 6:
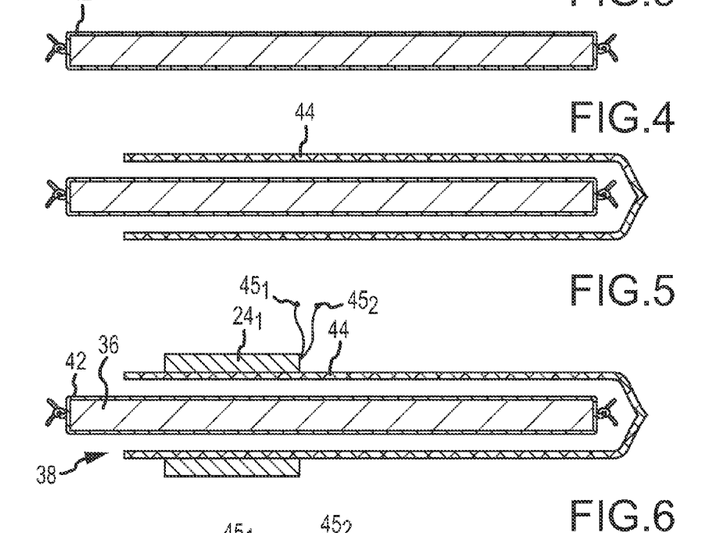

As shown in FIG. 4, an elongate inner liner 42 may then be placed on the mandrel 36. Once installed on the mandrel 36, inner liner 42 may be secured, for example, by knotting one or both ends. Inner liner may comprise polymeric materials, or may comprise polytetrafluoroethylene (PTFE).

As shown in FIG. 5, the next step may involve placing a sheath layer, such as a braid layer 44, over inner liner 42 to surround inner liner 42. Braid layer 44 may comprise conventional materials and construction approaches, such as, for example only, metal braid (e.g., 0.002" thick×0.006" wide wire woven in accordance with a known braid pattern), such as stainless steel. Braided wire in braid layer 44 may be rounded wire, flat wire with a rectangular cross-section (i.e., taken along a plane orthogonal to axis "A"), or another appropriate wire known in the art.

Sensor $24_1$ may then be placed over braid layer 44 on or at distal end portion 38, as shown in FIG. 6. Sensor $24_1$ may be a coil sensor, including a tubular core and a wire coil wrapped on the core, or another suitable sensor known in the art. As shown, coil sensor $24_1$ includes a pair of free ends $45_1$ and $45_2$.

Figure 7:
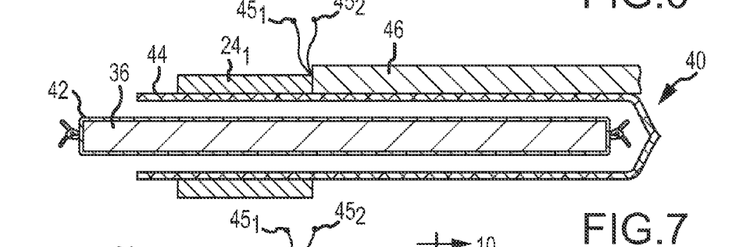

A longitudinally-extending element 46 may then be placed over braid layer 44, as shown in FIG. 7. Longitudinally-extending element 46 may extend from proximal end portion 40 to the proximal end of sensor $24_1$ and as described below is used to establish a path or conduit through an outer polymer layer (shown in FIG. 8) for one or more signal wires and/or one or more power wires in the finished medical device.

The construction of element 46 will vary between the first and second embodiments. In the first embodiment of the medical device, designated device 26a (best shown in FIG. 12a), longitudinally-extending element 46 is a tube configured to remain in place in the finished assembly. The tube includes a central passage through which connecting wires may be passed from the proximal end 40 of the device for electrical coupling to sensor $24_1$. In the second embodiment of the medical device, designated device 26b (best shown in FIG. 12b), longitudinally-extending element 46 is an elongate solid body configured to be removed from the outer layer of the finished assembly. Removal of the elongate solid body leaves a corresponding lumen extending longitudinally through the outer layer (jacket) and through which the connecting wires may be threaded from the proximal end 40 to be electrically coupled to sensor $24_1$. Such an elongate solid body may comprise, for example, but without limitation, a pin coated with PTFE. The pin is removed from proximal end 40 of finished device 26.

In any of the embodiments of device 26, the wiring 50 referred to herein for connecting to sensor $24_1$ may comprise an unshielded twisted-pair (TP) cable or alternately a shielded twisted-pair cable, or any other functionally equivalent signal or power cable known in the art comprising at least one wire. One or more of polymer, PTFE, and/or other appropriate materials may be included in wiring 50 for electrical insulation.

Figure 8:
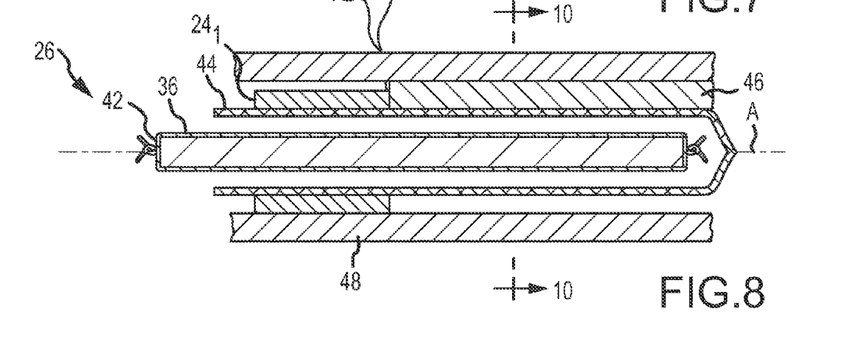

As shown in FIG. 8, an outer layer 48 is then applied over the sub-assembly thus formed. Outer layer 48 may comprise conventional melt processing polymers, such as, for example only, an elastomer commercially available under the trade designation PEBAX® from Arkema, Inc. Furthermore, outer layer 48 may comprise either a single section or multiple sections of tubing that are either butted together or overlapped with each other. The multiple segments, or layers, of outer layer material may be any length and/or hardness (durometer) allowing for flexibility of design, as known in the art. The distal end portion and proximal end portions of the device may be uncovered by outer layer 48. Free ends $45_1$, $45_2$ may be secured so as to not become embedded in outer layer 48. The distal end of element 46 is secured or protected so as to not receive melted (and thus fluid) melt polymer of outer layer 48. In an embodiment, a removable stop may be used.

The assembly thus formed is then subjected to a reflow lamination process, which involves heating the assembly until the outer layer material flows and redistributes around the circumference, covering and embedding braid layer 44, sensor $24_1$, and longitudinally-extending element 46. In one embodiment, the reflow process includes heating the device to about 450° F. (e.g., in an oven-like appliance), though the reflow temperature may vary for other embodiments of the method. Device 26 is then cooled. After cooling, outer layer 48 may be a unitary jacket 48. The distal and proximal end portions of device 26 may then be finished in a desired fashion. It should be understood that as used with reference to a medical device herein, "distal" refers to an end that is advanced to the region of interest within a body while "proximal" refers to the opposite end that is disposed outside of the body and manipulated manually by a clinician or automatically through, for example, robotic controls.

Figure 9:
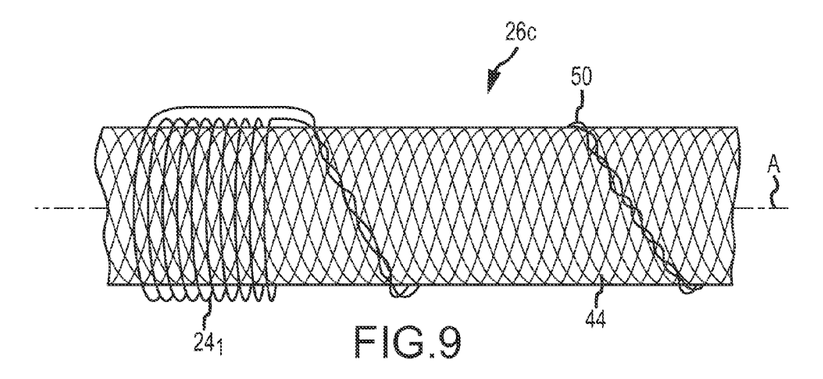
FIG. 9 is an isometric view of a third embodiment of an MPS-enabled elongate medical device at a stage of construction equivalent to that shown in FIG. 7.

FIG. 9 is an isometric view of an unfinished third embodiment of the medical device, designated device 26c (shown finished in FIG. 12c), at a stage of construction equivalent to that shown in FIG. 7. Rather than by using longitudinally-extending element 46 in the manufacturing process to provide a wire path or conduit, as described above, device 26c is constructed by winding one or more wires 50 directly on braid layer 44 and coupling one or more wires 50 to sensor $24_1$. In FIG. 9, one or more wires 50 may comprise a twisted-pair cable, which may be, as shown, wound helically about braid layer 44. It should be understood that variations are possible, and that other wiring configurations (e.g., those described above) may be used.

Figure 10:
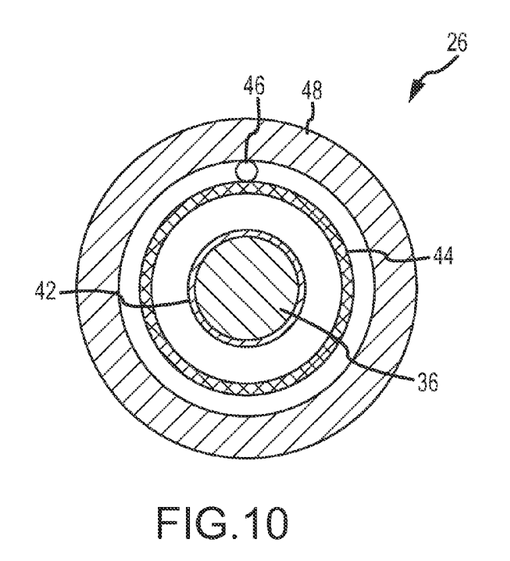
FIG. 10 is a cross-sectional view of an MPS-enabled elongate medical device, before a reflow lamination process, taken substantially along line 10-10 in FIG. 8.

FIG. 10 is a cross-sectional view of device 26 before reflow, taken substantially along line 10-10 in FIG. 8 (or taken at a point just proximal of sensor $24_1$ in FIG. 9). Inner liner 42 is wrapped around mandrel 36, and braid layer 44 is wrapped around inner liner 42. Although a radial clearance is shown between inner liner 42 and braid layer 44, braid layer 44 may also be disposed tightly on inner liner 42. Additionally, because braid layer 44 is flexible and braided, the size of any radial clearance between inner liner 42 and braid layer 44 may vary over the length of device 26 and may be circumferentially asymmetrical. Longitudinally-extending element 46 is disposed "on top of" (i.e. radially outward from) braid layer 44, and outer layer 48 encompasses the assembly. Further, element 46 extends generally parallel to the main, central axis of the device 26 (see axis "A" in FIGS. 8 and 9). It should be noted that although FIG. 10 is a cross-section of the assembly in FIG. 8, which illustrates the first and second embodiments of device 26, FIG. 10 also illustrates the third embodiment, device 26c, as indicated above.

Figure 11:
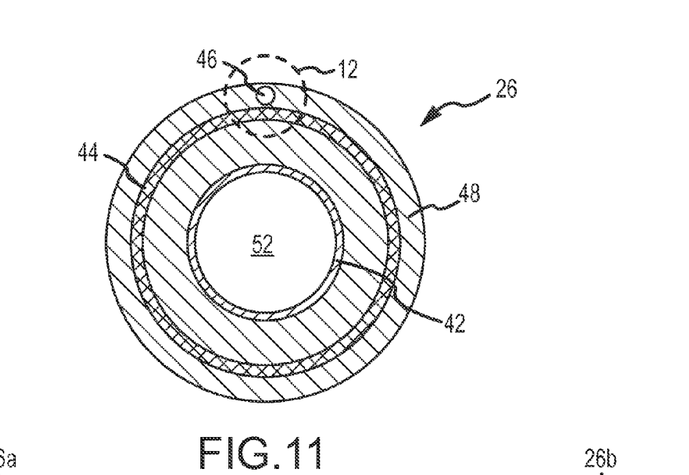
FIG. 11 is the cross-sectional view of FIG. 10, after a reflow lamination process.

FIG. 11 is the cross-sectional view of FIG. 10 after a reflow lamination process. Outer layer 48 has flowed into the rest of the assembly and fused to form jacket 48, embedding longitudinally-extending element 46 and braid layer 44 and filling space between longitudinally-extending element 46 and braid layer 44. Outer layer 48 has also flowed through braid layer 44 into any clearance between braid layer 44 and inner liner 42. Inner liner 42 and/or mandrel 36 are impervious to the flow of outer layer 48, so jacket 48 remains radially outward from inner liner 42. As a result, when mandrel 36 is removed after the reflow process, a central lumen 52 remains Like FIG. 10, FIG. 11 also illustrates the third embodiment—device 26c— by replacing longitudinally-extending element 46 with one or more wires 50.

Figure 12A:
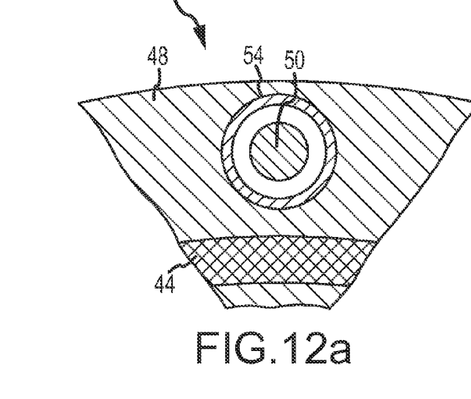
FIG. 12a is an expanded view of a portion of the cross-section of FIG. 11, illustrating the first embodiment of an MPS-enabled elongate medical device.
Figure 12B:
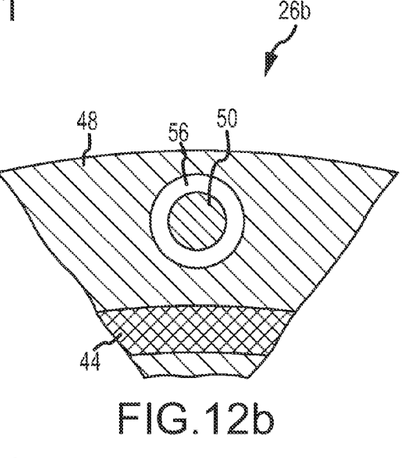
FIG. 12b is an expanded view of a portion of the cross-section of FIG. 11, illustrating the second embodiment of an MPS-enabled elongate medical device.
Figure 12C:
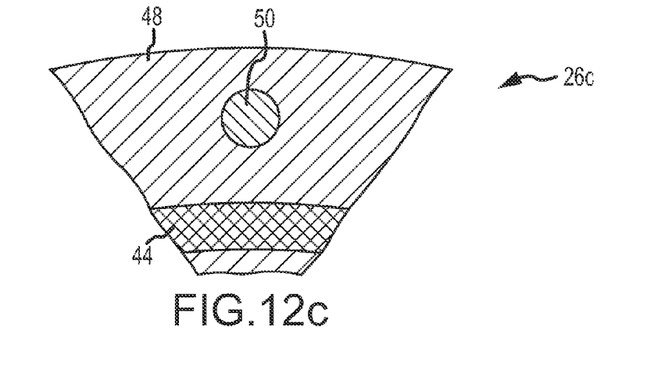
FIG. 12c is an expanded view of a portion of the cross-section of FIG. 11, illustrating the third embodiment of an MPS-enabled elongate medical device.

FIGS. 12a, 12b, and 12c are expanded views of the three embodiments 26a, 26b, and 26c described above. In particular, FIG. 12c shows a portion of the third embodiment of FIG. 11, indicated by circle 12.

FIG. 12a illustrates device 26a, in which longitudinally-extending element 46 is a tube 54. Tube 54 is embedded in jacket 48, radially outward from braid layer 44. In an exemplary embodiment, tube 54 is embedded such that it is completely covered circumferentially by jacket 48, and is completely covered along its axial length by jacket 48. One or more wires 50 are provided to extend longitudinally (i.e., substantially parallel with axis "A") through tube 54 to sensor $24_1$ and may be coupled to sensor $24_1$. In this regard, note that the removable stop, if used, must be removed from the distal end of tube 54, and free ends $45_1$, $45_2$ of coil sensor $24_1$ are electrically connected to wiring 50 (e.g., TP cable). The wiring 50/sensor $24_1$ connection is then embedded in the surface of outer layer 48 and is otherwise suitably finished. Tube 54 may comprise polyimide or another material able to withstand the temperatures required for the reflow process without substantially deforming (i.e. a material with a higher melting point than the material used for jacket 48). In one embodiment, tube 54 may have an inner diameter of about 0.006 inches, or about 150 micrometers, an outer diameter of about 0.008 inches, or about 200 micrometers, and a wall thickness of about 0.001-0.002 inches, or about 25-50 micrometers, though the dimensions of tube 54 may change as needed for a particular device or application.

FIG. 12b illustrates device 26b. In the second embodiment, longitudinally-extending element 46 is a pin or other elongate member, which may be coated with PTFE or another lubricant configured to facilitate removal of the pin (or member) after reflow. The pin is removed from jacket 48 after the reflow process, preferably taken or drawn from proximal end 40 of the device. A longitudinally-extending (i.e., substantially parallel with axis "A") wiring lumen 56 remains in jacket 48 after the pin is removed, through which one or more wires 50 may be provided for coupling to sensor $24_1$. As in device 26a, free ends $45_1$, $45_2$ of coil sensor $24_1$ in device 26b are electrically connected to wiring 50 (e.g., TP cable). The wiring 50/sensor $24_1$ connection is then embedded in the surface of outer layer 48 and is otherwise suitably finished. The inner wall of wiring lumen 56 comprises the material of jacket 48.

FIG. 12c illustrates device 26c, previously shown in FIG. 9. One or more wires 50 are embedded directly in jacket 48, having been wrapped directly on braid layer 44. It should be understood that the free ends of wiring 50 at the proximal end (not shown in FIG. 9) of device 26c will remain free during the reflow process, and steps are taken to ensure that such free ends are not embedded in outer layer 48.

The method of manufacturing medical device 26 described in connection with FIGS. 3-12 provides many benefits. Because sensor $24_1$, braid layer 44, and one or more wires 50 are embedded in jacket 48, device 26 has a smooth exterior with a relatively constant outer diameter. A constant and uniform outer diameter advantageously allows device 26 to be advanced and withdrawn through other devices, such as an introducer for example, and likewise have other devices extend and be advanced and withdrawn over device 26. In addition, further exterior layers may be added to device 26. Embedding one or more wires 50 in jacket 48 minimizes the effect of one or more wires 50 on the mechanical properties of device 26 and minimizes the stress induced on wiring 50 by bending of the medical device. Additionally, because device 26 is manufactured using a mandrel, as described above, device 26 may be easily fabricated to have a central lumen for the passage of materials, fluids and other devices, as known in the art.

Device 26 may also be manufactured through an alternate second method. In the second method, the sub-assembly comprising mandrel 36, inner liner 42, braid layer 44, sensor $24_1$, and longitudinally-extending element 46 is dipped in a polymer dip solution. After the assembly is dipped, the polymer dip layer is cured, thereby encapsulating the sub-assembly. Outer layer 48 may then be added and reflow may be performed to finish device 26. The alternate method of manufacture may more reliably fill voids in the sub-assembly, but has the most benefit in those applications where a decreasing durometer shaft along the device's longitudinal length towards the distal end is not desired or required, since the dip process results in a more uniform durometer shaft (outer body or layer) as a function of the device's length.

Figure 13:
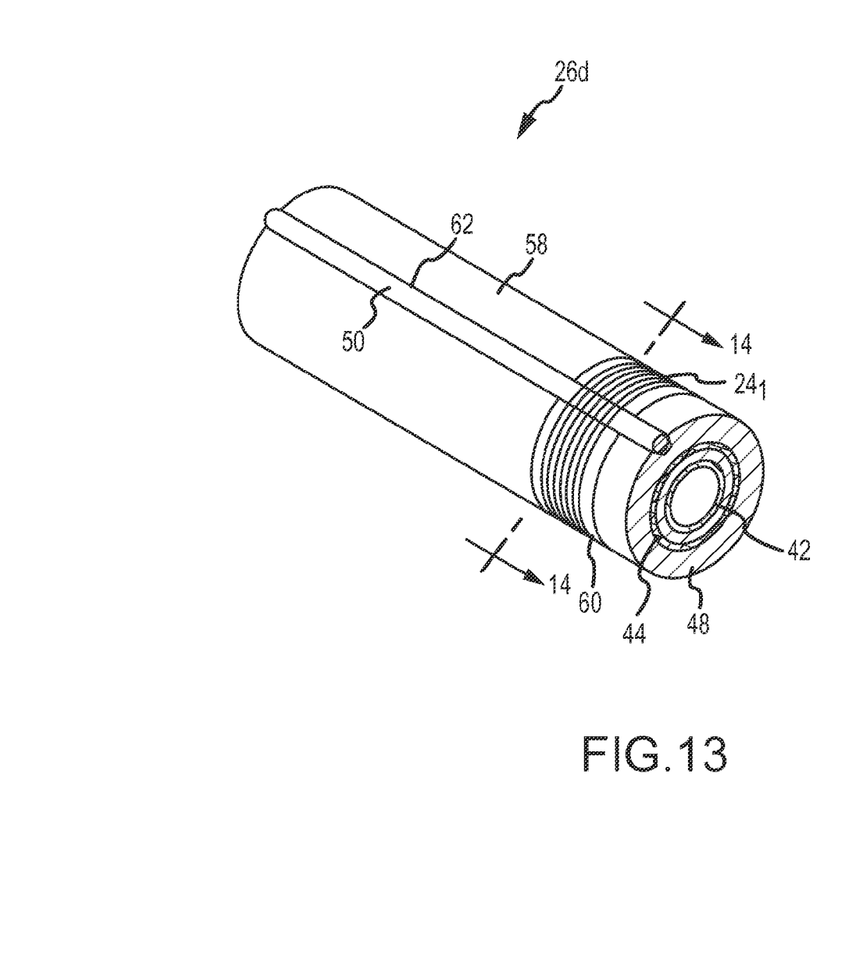
FIG. 13 is an isometric view of a fourth embodiment of an MPS-enabled elongate medical device.

FIG. 13 is an isometric view of a fourth embodiment of an MPS-enabled elongate medical device, designated device 26d. Inner liner 42 and braid layer 44 are substantially the same as in the first three embodiments, devices 26a, 26b and 26c. Jacket 48 has been altered relative to the other three embodiments to have an outer surface 58 with a circumferentially-extending sensor groove 60 and a longitudinally-extending wire groove 62. Sensor $24_1$ is disposed in sensor groove 60, and one or more wires 50 are disposed in wire groove 62. Wiring 50 is electrically coupled to sensor $24_1$. In FIG. 13, sensor $24_1$ is a coil sensor. Sensor groove 60, and therefore sensor $24_1$, may be placed on any part of device 26d where a P&O may be desired or required for purposes known in the art (e.g., navigation or mapping).

Device 26d may be manufactured by a method similar to the method used for the first three embodiments—devices 26a, 26b and 26c. Inner liner 42, braid layer 44, and outer layer 48 may all be placed on a mandrel and subjected to a reflow process. Sensor groove 60 and wire groove 62 may be formed in outer surface 58 before reflow, then outer layer 48 may be prevented from flowing back into the grooves. Sensor $24_1$ and one or more wires 50 may be added to sensor groove 60 and wire groove 62, respectively, after reflow. Sensor $24_1$ and one or more wires 50 may then be fixed in place by applying, for example, but without limitation, adhesive, silicone coating, a heat shrink layer, or another appropriate fixation means.

Figure 14:
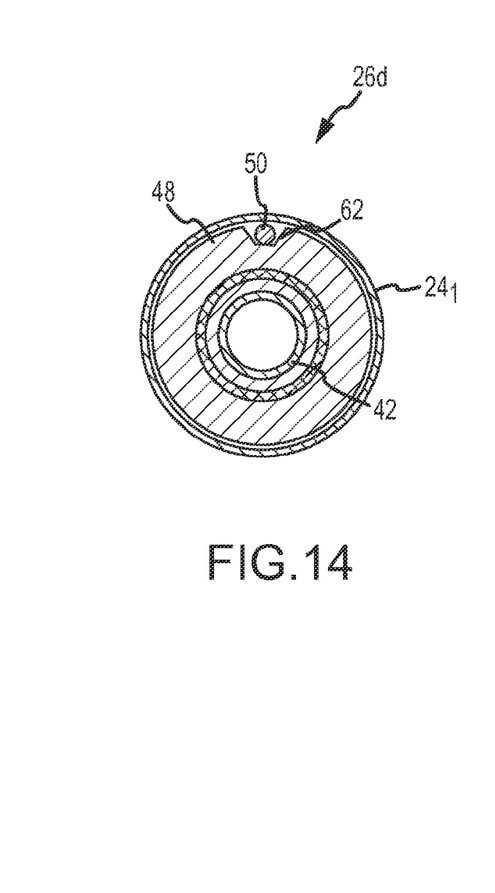
FIG. 14 is a cross-sectional view of the fourth embodiment, taken substantially along line 14-14 in FIG. 13.

FIG. 14 is a cross-sectional view of device 26d, taken substantially along line 14-14 in FIG. 13. The radial depth of wire groove 62 is greater than the radial depth of sensor groove 60; thus, one or more wires 50 may pass underneath sensor $24_1$ or be coupled to the underside of sensor $24_1$. In other words, one or more wires 50 may be radially inward from at least a portion of sensor $24_1$, for extension past sensor $24_1$ and/or for coupling with sensor $24_1$.

Figure 15:
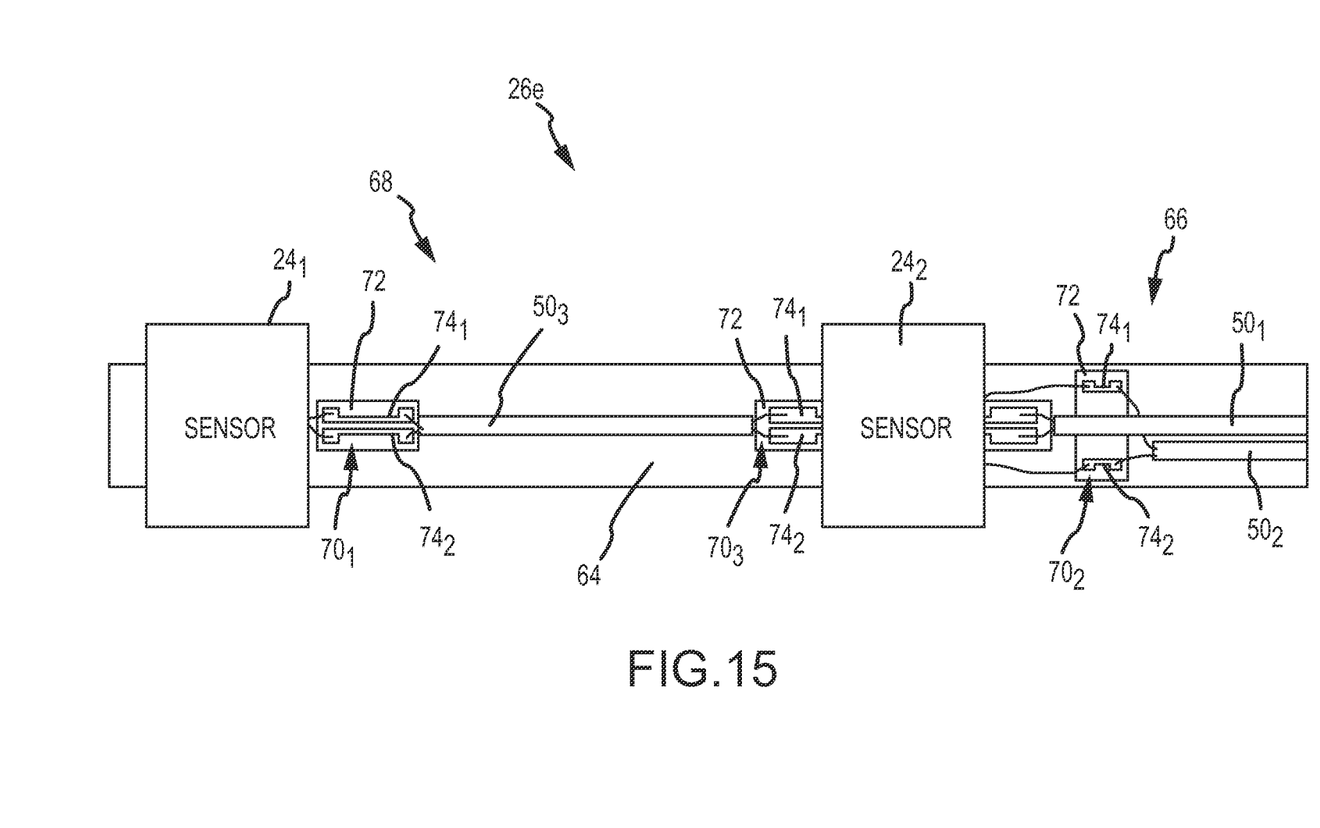
FIG. 15 is a diagrammatic view of a fifth embodiment of an MPS-enabled elongate medical device.

FIG. 15 is a diagrammatic view of a fifth embodiment of an MPS-enabled elongate medical device, designated device 26e. Device 26e may comprise a variety of medical devices, such as a catheter or an introducer. Device 26e has a body portion 64 with a proximal end portion 66 and a distal end portion 68, two coil sensors $24_1$, $24_2$, and wiring $50_1$, $50_2$, and $50_3$. Wiring $50_1$, $50_2$, and $50_3$ may comprise, for example, twisted pair (TP) cable, as described herein. Wiring $50_1$ and intermediate wiring piece $50_3$ provide electrical connectivity between the proximal end of device 26e and sensor $24_1$. Wiring $50_2$ provides electrical connectivity between the proximal end of device 26e and sensor $24_2$. Wiring $50_1$, $50_2$, may be incorporated into device 26e according to one of the previous embodiments described herein. Each of the wiring $50_1$, $50_2$, portions extend to the proximal end of the device 26e for connection to a connector or the like. As described elsewhere herein, such a connector may be coupled to MPS 20, where the respective signals detected by coils $24_1$, $24_2$, (respectively carried by wiring $50_1$, $50_2$, portions) may be processed by MPS 20 to determine respective position and orientation parameters associated with coils $24_1$, $24_2$.

Device 26e further includes three flexible circuits 70 for routing electrical signals. Flex circuits $70_1$ and $70_3$ each comprise an electrically-insulative substrate 72 and one or more electrically-conductive traces 74. Each trace 74 includes a relatively large contact pad at both its distal end and its proximal end. Referring to circuit $70_1$, leads from coil sensor $24_1$ (i.e., free ends of the wire wound to form the coil) are electrically coupled (e.g., by soldering) to the respective distal contact pads of traces $74_1$, $74_2$. Leads from the distal end of intermediate wiring segment $50_3$ are electrically coupled to the respective proximal contact pads of traces $74_1$, $74_2$ on flex circuit $70_1$. As a result, flex circuit $70_1$ provides electrical connectivity between sensor $24_1$ and intermediate wiring segment $50_3$.

Similarly, flex circuit $70_3$ provides electrical connectivity between wiring $50_1$ and wiring $50_3$. Leads from wiring $50_1$ are electrically coupled to respective proximal contact pads of traces $74_1$, $74_2$ on circuit $70_3$. Leads from wiring $50_3$ are electrically coupled to respective distal contact pads of traces $74_1$, $74_2$ on circuit $70_3$. Flex circuit $70_3$ is disposed radially-inwardly from sensor $24_2$, so flex circuit $70_3$ acts as an "electrical underpass" for routing an electrical signal detected by the sensor $24_1$ from the distal side of sensor $24_2$ (intermediate wiring $50_3$) to the proximal side of sensor $24_2$ (wiring 500.

Flex circuit $70_2$ provides electrical connectivity between wiring $50_2$ and sensor $24_2$. Flex circuit $70_2$, like $70_1$ and $70_3$, includes an electrically-insulative substrate 72 and a plurality of traces 74.

In the manufacturing process, flex circuits 70 may be bonded to body portion 64 before the addition of coil sensors 24. Flex circuits 70 are significantly thinner than wiring 50, so routing the signal detected by sensor $24_1$ through the flex circuit $70_3$ (and under sensor $24_2$) results in less radial bulk than simply disposing a segment of wiring 50 radially-inwardly of sensor $24_2$. Therefore, flex circuits 70 provide a means to incorporate two or more sensors on device 26e without appreciably increasing the radial thickness of device 26e as compared to a single-sensor device.

In another embodiment of device 26e, wiring $50_3$, flex pad $70_1$, and flex pad $70_3$ can be combined into a single longer flex circuit, minimizing cable lead exposure and termination procedures during manufacturing. In another embodiment, flex circuit $70_2$ may be combined with flex circuit $70_3$ to form a flex circuit with a substrate 72, four total traces 74, six contact pads on the proximal side of sensor $24_2$ (two for wiring $50_1$, two for wiring $50_2$, and two for sensor $24_2$), and two contact pads on the distal side of sensor $24_2$. In yet a further embodiment, flex circuits $70_1$, $70_2$, and $70_3$ and wiring $50_3$ may all be combined into a single flex circuit.

Figure 16:
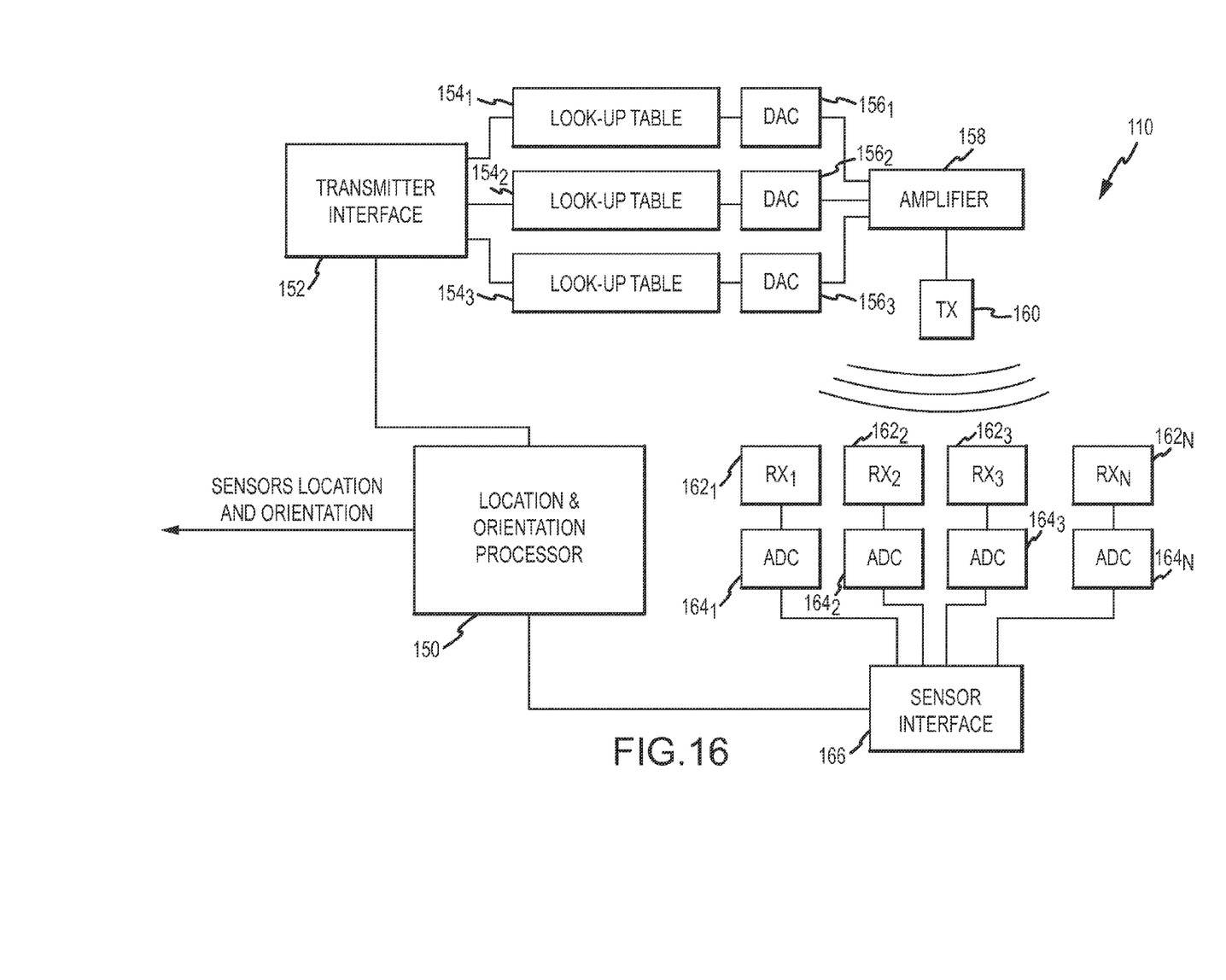
FIG. 16 is a schematic and block diagram view of one exemplary embodiment of a medical positioning system (MPS) as shown in block form in FIG. 1.

FIG. 16 is a schematic and block diagram of one exemplary embodiment of MPS 20, designated as an MPS 108, as also seen by reference to U.S. Pat. No. 7,386,339, referred to above, and portions of which are reproduced below, which generally describes, at least in part, the gMPS™ medical positioning system commercially offered by MediGuide Ltd. of Haifa, Israel and now owned by St. Jude Medical, Inc. It should be understood that variations are possible, for example, as also seen by reference to U.S. Pat. No. 6,233,476 entitled MEDICAL POSITIONING SYSTEM, also hereby incorporated by reference in its entirety. Another exemplary magnetic field-based MPS is the Carto™ system commercially available from Biosense Webster, and as generally shown and described in, for example, U.S. Pat. No. 6,498,944 entitled "Intrabody Measurement," and U.S. Pat. No. 6,788,967 entitled "Medical Diagnosis, Treatment and Imaging Systems," both of which are incorporated herein by reference in their entireties. Accordingly, the following description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that system 10, particularly main control 12, as described above may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An elongate medical device having a longitudinal axis, said medical device comprising:
   a body portion having a distal end portion and a proximal end portion;
   a first sensor;
   a second sensor located axially-proximally of said first sensor;
   a first set of one or more wires configured to carry an electrical signal from said proximal end portion to a first point axially-proximal of said second sensor;
   a second set of one or more wires configured to carry said electrical signal from a second point axially-distal of said second sensor to said first sensor; and
   a flex circuit disposed radially-inwardly from said second sensor, said flex circuit comprising a flexible electrically-insulative substrate and an electrically-conductive trace disposed on said substrate, wherein said trace is configured to provide an electrical connection between said first set and said second set.

2. The elongate medical device of claim 1, wherein said second sensor is a coil sensor.

3. The elongate medical device of claim 1, wherein said first sensor is a coil sensor.

4. The elongate medical device of claim 1, wherein said trace comprises a first contact pad configured to be electrically coupled with said first set and a second contact pad configured to be electrically coupled with said second set.

5. The elongate medical device of claim 1, wherein said flex circuit further comprises a second electrically-conductive trace.

* * * * *